United States Patent
Batzer et al.

(10) Patent No.: US 9,872,629 B2
(45) Date of Patent: Jan. 23, 2018

(54) REJECTION OF THE COMMON-MODE SIGNAL COMPONENT IN THE MEASUREMENT OF BIOELECTRIC SIGNALS

(71) Applicants: Ulrich Batzer, Buckenhof (DE); Peter Greif, Pinzberg/Gosberg (DE); Harald Karl, Fürth (DE)

(72) Inventors: Ulrich Batzer, Buckenhof (DE); Peter Greif, Pinzberg/Gosberg (DE); Harald Karl, Fürth (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 15/014,233

(22) Filed: Feb. 3, 2016

(65) Prior Publication Data
US 2016/0228024 A1    Aug. 11, 2016

(30) Foreign Application Priority Data
Feb. 11, 2015   (DE) .................. 10 2015 202 447

(51) Int. Cl.
*A61B 5/04*    (2006.01)
*A61B 5/0428*    (2006.01)
*G01R 19/00*    (2006.01)
*A61B 5/0408*    (2006.01)
*A61B 5/00*    (2006.01)
*G01R 19/10*    (2006.01)

(52) U.S. Cl.
CPC .......... *A61B 5/0428* (2013.01); *A61B 5/0408* (2013.01); *A61B 5/7203* (2013.01); *G01R 19/0084* (2013.01); *G01R 19/10* (2013.01)

(58) Field of Classification Search
CPC ... A61B 5/0428; A61B 5/0408; A61B 5/7203; G01R 19/0084; G01R 19/10

USPC ............... 600/509, 515, 516, 517, 519, 521
See application file for complete search history.

(56) References Cited

U.S. PATENT DOCUMENTS

| | | | | |
|---|---|---|---|---|
| 5,392,784 A | * | 2/1995 | Gudaitis | A61B 5/0428 128/902 |
| 2003/0073916 A1 | * | 4/2003 | Yonce | A61B 5/0428 600/509 |

FOREIGN PATENT DOCUMENTS

DE    4417609 A1    2/1995

OTHER PUBLICATIONS

German Office action for related German Application No. 10 2015 202 447.4, dated Sep. 29, 2015, with English Translation.

* cited by examiner

*Primary Examiner* — Michael Carey
(74) *Attorney, Agent, or Firm* — Lempia Summerfield Katz LLC

(57) ABSTRACT

A differential voltage measuring system is described. The differential voltage measuring system has a signal measuring circuit for measuring bioelectric signals, and an interference-signal measuring circuit coupled to the potential of the differential voltage measuring system and electrically connected to a fixed reference potential. In this case, the interference-signal measuring circuit is designed for measuring a current flowing from the potential of the differential voltage measuring system to the fixed reference potential. A differential voltage measuring system with an additional path is also described. Furthermore, a differential voltage measuring system with an averaging potential measuring method is described.

19 Claims, 4 Drawing Sheets

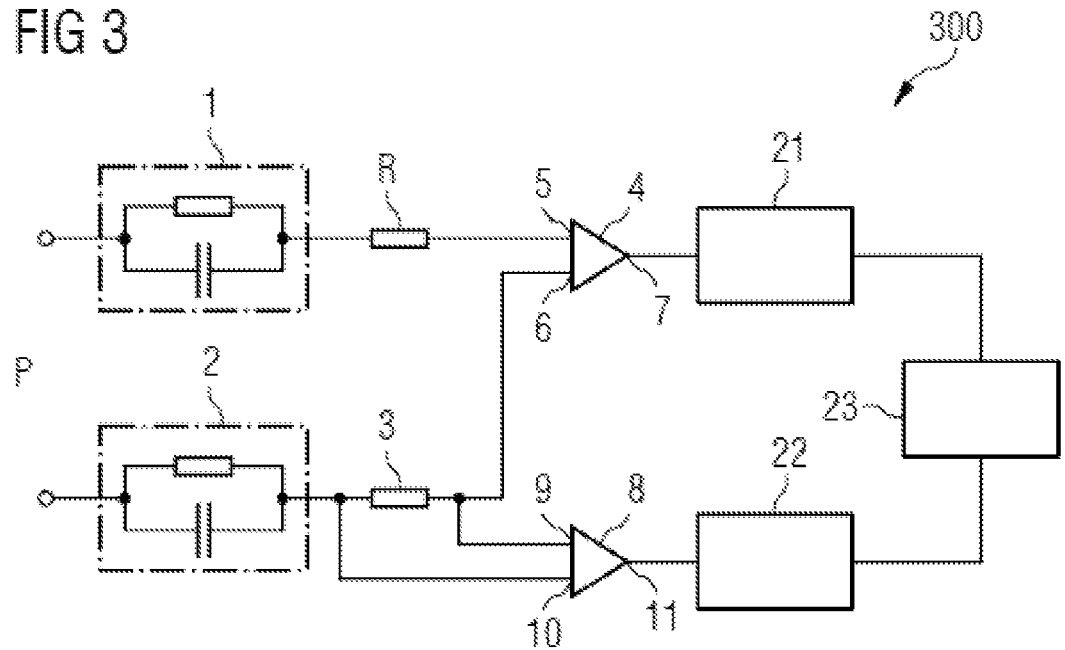
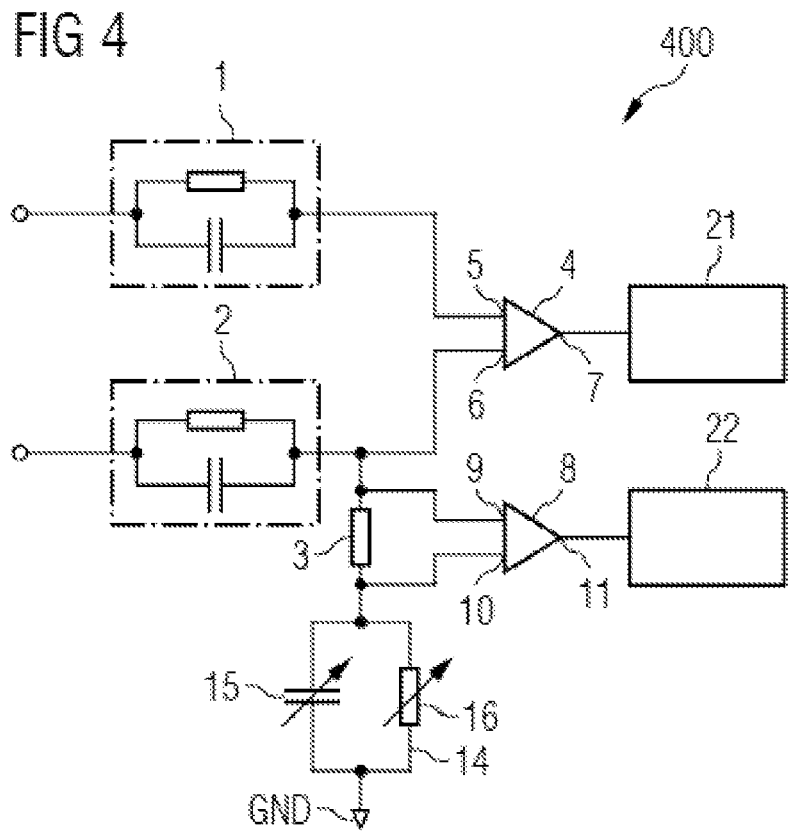

REJECTION OF THE COMMON-MODE SIGNAL COMPONENT IN THE MEASUREMENT OF BIOELECTRIC SIGNALS

This application claims the benefit of DE 10 2015 202 447 A1, filed on Feb. 11, 2015, which is hereby incorporated by reference in its entirety.

TECHNICAL FIELD

The embodiments relate to a differential voltage measuring system and to a method for differentially measuring voltages of bioelectric signals.

BACKGROUND

During the measurement of bioelectric signals, (e.g., of ECG signals), common-mode interference signals (e.g., interference as a result of common-mode signals) occur as a result of non-ideal measurement inputs of an ECG measuring arrangement. These signals arise, for example, from the power supply frequency at 50 Hz. Common-mode interference signals occur if non-identical conditions such as different impedances and capacitances occur at the two measurement inputs during the differential ECG signal measurement. An example of a conventional measuring arrangement for measuring an electrocardiogram is depicted in FIG. 1.

Common-mode signals, (e.g., interference signals), are not concomitantly amplified during the differential measurement, and so they are rejected. The different impedances of the inputs of the ECG measuring arrangement have the effect that different input signals caused by the same interference signal are present at the two inputs of an amplifier circuit of an ECG measuring arrangement, and so the interference signal is amplified together with the actual measurement signal. These common-mode interference signals are very strong in the application on a patient, (for example, a human being or an animal), since the electrode contacts on the patient's skin vary greatly in quality without complex preparation. An electrode contact on the patient may have impedances of between 10 kohms and several megaohms and likewise greatly varying capacitances. As a result, the difference between the impedances and capacitances at two measurement inputs is also in the range of up to several megaohms. An example of an ECG signal subjected to common-mode interference due to an impedance difference of 500 kohms is depicted in FIG. 2. In some instances, the differences in impedance at the inputs of the ECG measuring arrangement are even higher, such that an evaluation of the ECG signal scarcely appears to be possible any longer.

A possible circuit with which the described common-mode interference signals may be determined and rejected is described in German patent application DE 10 2014 219 943 A1. The measuring circuit described in the cited patent application (see FIG. 3) has a first measuring path and a second measuring path. It has in one of the two measuring paths, for example, the second measuring path, a shunt resistor. A voltage drop that is proportional to the common-mode current flowing in the second measuring path occurs at the shunt resistor. In addition, the arrangement includes an adaptive filter, which is set in accordance with the voltage drop detected and filters the detected measurement signal in such a way that the common-mode component of the measurement signal detected is rejected.

The shunt resistor influences the measurement signals detected by way of the amplifier circuit by thermal noise, however.

An alternative arrangement in German patent application DE 10 2014 219 943 A1 includes a shunt resistor in an additional measuring path that is separate from the second measuring path or branches off from it (see FIG. 4). Since in the case of this variant the shunt resistor does not lie directly in the second measuring path, it also does not influence the measurement signals detected by way of the first amplifier circuit by thermal noise.

A problem with the arrangements described is that the adaptive filtering used therein also leads to an attenuation of the useful signal, which reduces the overall gain of the signal/noise ratio. Furthermore, also in the case of the circuit arrangement depicted in FIG. 4, there is still a direct electrical connection between the shunt resistor for measuring the common-mode signals and the second measuring path, even if in this case the shunt resistor is not integrated in the second measuring path directly or in series. The shunt resistor therefore still lies in the range of influence of the analog input circuitry, and so there is still a certain remaining interfering interaction between the measuring arrangement for measuring the common-mode currents and the measuring circuit for measuring the useful signals.

SUMMARY AND DESCRIPTION

The scope of the present invention is defined solely by the appended claims and is not affected to any degree by the statements within this summary. The present embodiments may obviate one or more of the drawbacks or limitations in the related art.

It is therefore an object of the present embodiments to develop a differential voltage measuring system with an improved signal/noise ratio in which the interferences due to common-mode signals are effectively rejected.

This object is achieved by a differential voltage measuring system, by a differential voltage measuring system with an additional path with a driver circuit for the right leg, or by a differential voltage measuring system with an averaging potential measuring method.

The differential voltage measuring system has a signal measuring circuit for measuring bioelectric signals, which is, for example, integrated in an ECG component. Furthermore, the differential voltage measuring system has an interference-signal measuring circuit, which is coupled to the potential of the differential voltage measuring system or the ECG component and is additionally electrically connected to a fixed reference potential. In this case, the interference-signal measuring circuit is designed for measuring a current flowing from the potential of the differential voltage measuring system to the fixed reference potential.

There is no direct coupling between the signal measuring circuit and the interference-signal measuring circuit. The two circuits are only connected by way of the potential of the signal measuring circuit or the ECG component.

The measurement of the current between the potential of the differential voltage measuring system and the fixed reference potential may be realized, for example, by an impedance being connected between the potential of the differential voltage measuring system and the fixed reference potential and having a differential amplifier circuit connected in parallel with it as a voltage measuring unit.

The impedance, which includes, for example, a capacitance, serves the purpose of converting the current flowing to the fixed reference potential into a measurable electrical voltage. The common-mode current flows from the electrodes into the ECG component. Only there does the current arrive in the signal measuring circuit and flow further to the potential of the ECG component on account of parasitic effects. From the potential of the ECG component, the current flows further in the direction of the fixed reference potential, for example, the connection to ground. Offering an explicit path on which the current flows from the potential of the ECG component in the direction of the connection to ground here allows a current flow to be measured on this path. The residual current flow from the ECG component to the connection to ground also again only takes place due to parasitic effects. The current between the signal measuring circuit or the ECG component and the interference-signal measuring circuit therefore only flows by way of the common potential of the ECG circuit.

Coupling the signal measuring circuit and the interference-signal measuring circuit only by way of the common potential of the ECG circuit achieves the effect of an optimum separation of the two subsystems, the influence of the interference-signal measuring circuit on the signal measuring circuit in particular being minimal.

A further separation of the detection of the measurement signal or the bioelectric signal from the patient and the measurement of the common-mode interference signal is therefore achieved, and so the measurement of the interference signal in common mode no longer impairs the measurement of the bioelectric signal.

The differential voltage measuring system with an additional path with a driver circuit for the right leg has a first measuring path, which includes a first electrode, which at the input is connected to a patient and at the output provides a first measuring contact. Moreover, the differential voltage measuring system with an additional path with a driver circuit for the right leg has a second measuring path, which includes a second electrode, which at the input is connected to the patient and at the output provides a second measuring contact. Part of the differential voltage measuring system is also an amplifier circuit with a first input, which is electrically connected to the first measuring path, and a second input, which is electrically connected to the second measuring path, and an output. The differential voltage measuring system has a first signal detection unit at the output of the amplifier circuit and an additional path with a contact with the patient. The additional path includes a driver circuit for the right leg, a shunt resistor with a known resistance value, which is connected between the additional contact and the driver circuit, and a voltage measuring device, which is connected parallel to the shunt resistor and with which the electrical voltage dropping across the shunt resistor, and consequently the current flowing between the additional contact and the driver circuit, may be measured.

A shunt resistor may refer to a low-impedance electrical resistance, which is used for measuring an electrical current flowing through it.

A driver circuit for the right leg, also referred to as the right-leg drive, may refer to a driver circuit that is connected to the patient by way of an additional path. The patient is set to a reference potential by way of the additional path, also referred to as the RLD path. The driver circuit serves for generating a signal that may be controlled to the average common-mode voltages of individual signals or all the signals of the individual measuring paths or may be set to a fixed voltage value. The measurement by way of the additional path, also known as the RLD path, has the advantage that the current is stronger there by one to three orders of magnitude than the current flowing through the first measuring path and the second measuring path.

The differential voltage measuring system with an averaging potential measuring method has a first measuring path, which includes a first electrode, which at the input is connected to a patient and at the output provides a first measuring contact. It has a second measuring path, which includes a second electrode, which at the input is connected to the patient and at the output provides a second measuring contact. Furthermore, the differential voltage measuring system has an amplifier circuit with a first input, which is electrically connected to the first measuring path, and a second input, which is electrically connected to the second measuring path, and an output. In addition, the differential voltage measuring system includes a first signal detection unit at the output of the amplifier circuit and a potential measuring unit, which is designed for determining an average value from a potential at the first measuring path between the first electrode and the first input of the amplifier circuit and a potential at the second measuring path between the second electrode and the second input of the amplifier circuit. This averaging has the advantage of thereby eliminating differential components caused by the different quality of the contacts of the electrodes of the first and second measuring paths at the common contact point at which the potential measuring unit measures.

In one refinement of the differential voltage measuring system, the signal measuring circuit has a first measuring path, which includes a first electrode, which at the input is connected to a patient and at the output provides a first measuring contact. The differential voltage measuring system also has a second measuring path, which includes a second electrode, which at the input is connected to the patient and at the output provides a second measuring contact. In this refinement, the signal measuring circuit has an amplifier circuit with a first input, which is electrically connected to the first measuring path, and a second input, which is electrically connected to the second measuring path, and an output. Furthermore, the signal measuring unit includes a first signal detection unit at the output of the amplifier circuit.

In a refinement of the differential voltage measuring system, the interference-signal measuring circuit has an amplifier circuit with a first input, which is electrically connected to the end of the impedance that is facing the potential of the differential voltage measuring system, and a second input, which is electrically connected to the end of the impedance that is facing the fixed reference potential, and an output. Moreover, in this refinement, the interference-signal measuring circuit has a first signal detection unit at the output of the amplifier circuit of the interference-signal measuring circuit.

In a variant of the differential voltage measuring system, a capacitance, which includes an element with a parasitic capacitance or an electrostatic discharge (ESD) protection capacitor, is connected between the impedance and the fixed reference potential.

In certain examples, the capacitance has a capacitance value of less than 10 pF.

In addition, the differential voltage measuring system may have a further contact with the patient for generating a signal that may be controlled to the average common-mode voltages of individual signals or all the signals or may be set to a fixed voltage value. This additional path is an RLD path, which is electrically connected to the already mentioned driver circuit for the right leg. If a signal affected by an interference signal is suitably transmitted, (e.g., negatively correlated), from the RLD path to the patient, compensation for the interference signal may be obtained with the aid of the signal applied to the patient.

In the case of the differential voltage measuring system with a driver circuit for the right leg, the shunt resistor may have a resistance value in the range of 10-100 kΩ.

In a refinement of the differential voltage measuring system with a driver circuit for the right leg, the voltage measuring device has an amplifier circuit. The amplifier circuit has a first input, which is electrically connected to the end of the shunt resistor that is facing the driver circuit, a second input, which is electrically connected to the end of the shunt resistor that is facing the additional contact to the patient, and an output. The amplifier circuit may, for example, be designed as an operational amplifier, (in particular, a differential amplifier), with which voltage differences may be determined.

In a variant of the differential voltage measuring system with a driver circuit for the right leg, the voltage measuring device includes a signal detection unit, which is electrically connected to the output of the amplifier circuit of the voltage measuring device.

In a refinement of the differential voltage measuring system with an averaging measuring method, the potential measuring unit includes two parallel-connected potential measuring paths. The first potential measuring path includes a first contact, between the first electrode and the first input of the amplifier circuit, and a first resistor and the second potential measuring path includes a second contact, between the second electrode and the second input of the amplifier circuit, and a second resistor. In this case, the two parallel-connected measuring paths are brought together to a common averaged potential at a branching point of the parallel-connected measuring paths.

The potential measuring unit may have an amplifier circuit, which includes a first input, which is electrically connected to the branching point of the parallel-connected potential measuring paths, and a second input, which is electrically connected to a reference potential, and an output. In this case, the potential measuring unit is designed for determining an averaged differential signal of the measuring paths and of the reference potential.

In a variant of the differential voltage measuring system with an averaging measuring method, the potential measuring unit has a second signal detection unit, which is electrically connected to the output of the amplifier circuit of the potential measuring unit.

Furthermore, the differential voltage measuring system with an averaging measuring method may have an additional patient contact with a driver circuit for the right leg. In this case, the potential measuring unit includes an additional potential measuring path between the additional patient contact and the branching point, and so the potential at the additional patient contact is taken into account in the determination of the averaged potential.

In an effective refinement, the differential voltage measuring system may have at least one additional measuring path and at least one additional amplifier circuit of the signal measuring circuit that is connected in parallel with the amplifier circuit and has inputs for two signals in each case.

Furthermore, the differential voltage measuring system may include one or more upstream multiplexers, by which further measuring contacts may be connected to the first signal input and the second signal input of the amplifier circuit of the signal measuring circuit.

BRIEF DESCRIPTION OF THE DRAWINGS

FIG. 3 depicts an example of a circuit arrangement with which common-mode interference signals are rejected, determined and compensated.

FIG. 4 depicts a differential voltage measuring system with a shunt resistor according to an exemplary embodiment.

The same components are provided with identical designations here in the various figures.

DETAILED DESCRIPTION

Figure 1:
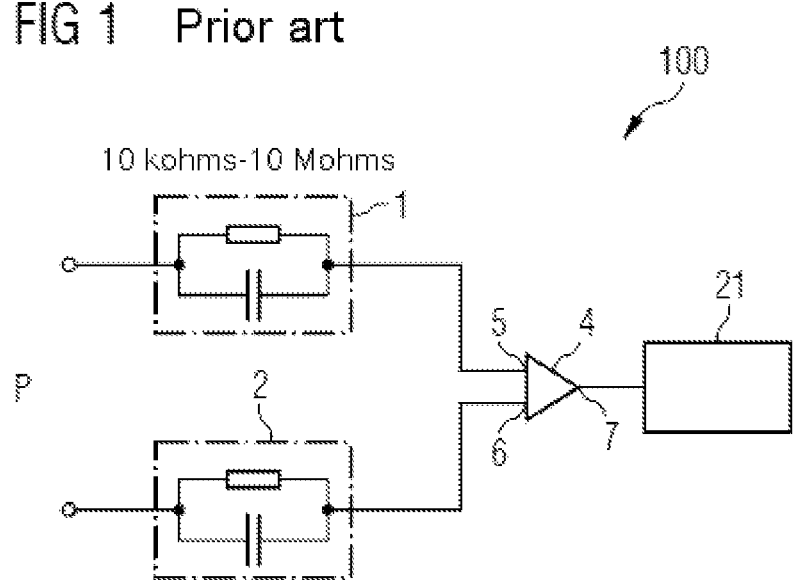
FIG. 1 depicts a block diagram of a conventional ECG measuring arrangement.

In FIG. 1, a conventional circuit arrangement 100 for measuring an electrocardiogram (ECG) of a patient P is depicted. The circuit arrangement 100 includes a first electrode 1 and a second electrode 2, which are in contact with the patient P in such a way that a cardiac current may flow by way of the electrodes 1, 2 to a differential amplifier 4. The amplifier 4 includes a first input 5, a second input 6 and an output 7. The first input 5 is electrically connected to the first electrode 1 and the second input 6 is electrically connected to the second electrode 2. The output signal of the amplifier 4 is transmitted to a signal detection unit 21, which detects the signal amplified by the amplifier 4. The two electrodes 1 and 2 are symbolized by an RC element, which illustrates the impedance values of the first measuring path and the second measuring path. In this case, the first measuring path runs from the contact of the first electrode 1 to the patient P by way of the first electrode 1 to the first input 5 of the amplifier 4 and the second measuring path runs from the contact of the second electrode 2 to the patient by way of the second electrode 2 to the second input 6 of the amplifier 4.

Figure 2:
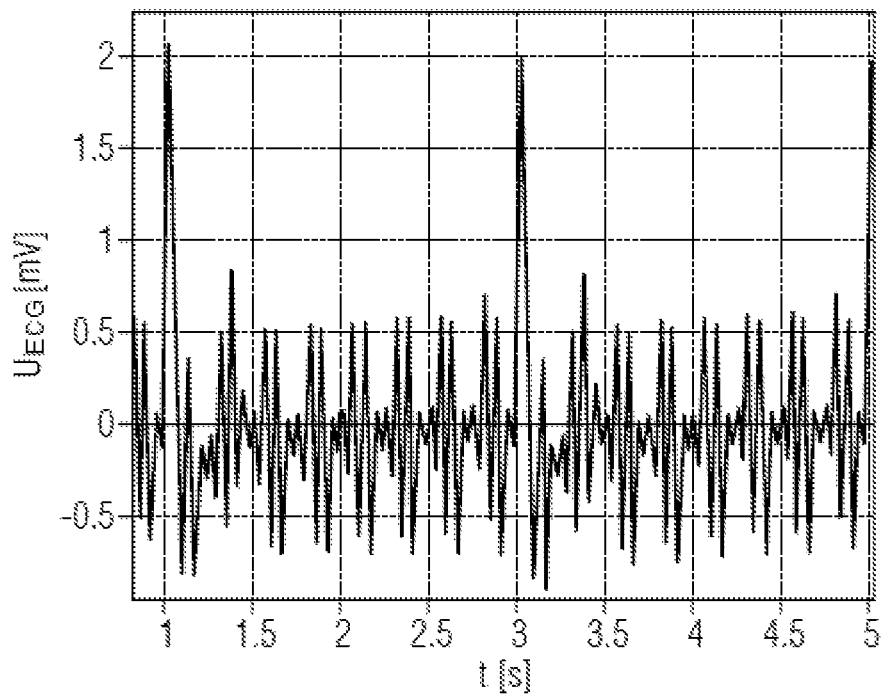
FIG. 2 depicts a diagram in which an ECG is superposed by interference signals.

An example of an ECG signal with common-mode interference caused by a difference in impedance of 500 kohms is depicted in FIG. 2. The associated test setup corresponds to the setup in FIG. 1. In the diagram shown, the amplitude $U_{ECG}$ of the ECG signal in mV is plotted against the time t in seconds. With a difference in impedance of 500 kohms, in the example the amplitude of the interference signals is about 1.3 mV. In this example, a strong ECG signal with an amplitude of more than 2 mV is obtained, but there are also patients with an amplitude of only 0.1 mV, which may be completely lost in this interference. In the case of greater differences in impedance, the amplitude of the common-mode interference signals increases further, and may even reach multiples of the representation shown.

In FIG. 3, a circuit arrangement 300 for differential measurements of ECG signals is illustrated.

A first electrode 1 is connected by its input to a patient P. The first electrode 1 is part of a first measuring path, which includes the first electrode 1 and additionally a resistor R. A second electrode 2 is likewise electrically connected by its input to the patient P. The second electrode 2 is connected by its output to a shunt resistor 3 and with it forms a second measuring path.

A first amplifier circuit 4 includes a first input 5 and a second input 6 and also an output 7. The first amplifier circuit 4 is connected by its first input 5 to the first electrode 1 by way of the resistor R. The first amplifier circuit 4 is electrically connected by its second input 6 by way of the shunt resistor 3 to the second electrode 2. The output 7 of the first amplifier circuit 4 is connected to an input of a signal detection unit 21. An output of the signal detection unit 21 is connected to an input of an evaluation unit 23.

A second amplifier circuit 8 includes a first input 9 and a second input 10, the first input 9 of the second amplifier circuit 8 being connected between the shunt resistor 3 and the second input 6 of the first amplifier circuit 4, and the second input 10 of the second amplifier circuit 8 being connected between the second electrode 2 and the shunt resistor 3. The second amplifier circuit 8 is electrically connected by its output 11 to a second signal detection unit 22.

While the first amplifier circuit 4 serves for detecting the measurement signals, (e.g., the cardiac currents of the patient), and passes on to the first signal detection unit 21 a signal corresponding to the difference between the signals detected by the first electrode 1 and the second electrode 2, which however possibly still has common-mode components, the second amplifier circuit 8 serves the purpose of determining a voltage drop across the shunt resistor 3 that is proportional to the common-mode current flowing in the second measuring path and passing it on to the second signal detection unit 22. The evaluation unit 23 may, for example, include an adaptive filter, which is set in accordance with the signal detected by the second signal detection unit 22 and filters the signal detected by the first signal detection unit 21 in such a way that the common-mode component of the measurement signal detected by the first signal detection unit 21 is rejected.

In FIG. 4, a circuit arrangement 400 with a shunt resistor 3 is depicted. In the case of this variant, the shunt resistor 3 is arranged in an additional measuring path that is separate from the second measuring path or branches off from it. A potential dropping across the shunt resistor 3 is measured by a second amplifier circuit 8 and passed on to a signal detection unit 22. Since, in the case of the variant depicted in FIG. 4, the shunt resistor 3 does not lie in the second measuring path, it also only influences the measurement signals detected by way of the first amplifier circuit 4 by thermal noise to a small extent. The additional measuring path for measuring the common-mode voltage also includes a controllable impedance 14 with a controllable capacitance 15 and a controllable ohmic resistance 16, it being possible for the controllable impedance 14 to be set, for example, in such a way that the additional measuring path for measuring the common-mode voltage has identical properties to the second measuring path. Alternatively, the controllable impedance 14 may also be set such that a higher current flow is achieved on the additional measuring path, which contributes to an improved rejection of common-mode interference signals on the first measuring path and the second measuring path. In the case of this signal measuring circuit, although the measuring path for the common-mode currents is already not directly in the signal measuring circuit, it is still in the range of influence of the analog input circuitry.

Figure 5:
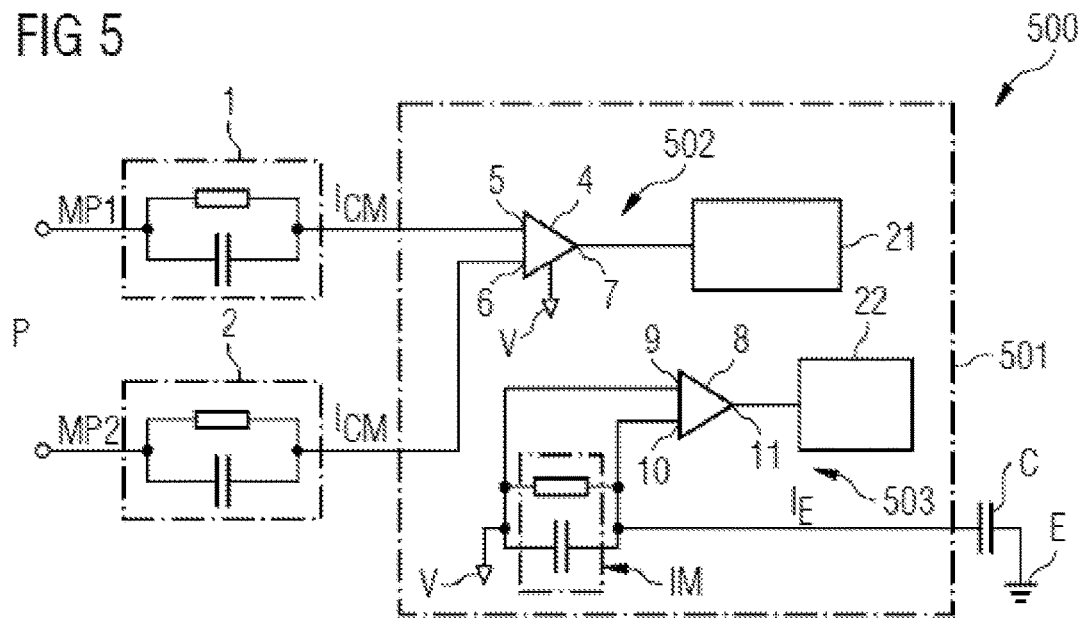
FIG. 5 schematically depicts a differential voltage measuring system according to a first exemplary embodiment.

In FIG. 5, a differential voltage measuring system 500 according to an exemplary embodiment, (for example, an ECG measuring circuit), is schematically illustrated. The differential voltage measuring system 500 includes two measuring paths MP1, MP2 and a signal measuring component 501, (for example, an ECG component), with two measuring circuits 502, 503. The first measuring circuit 502 is in this case a signal measuring circuit, with which, for example, an ECG signal affected by a common-mode current is measured. The second measuring circuit 503, also referred to hereinafter as the interference-signal measuring circuit, serves for measuring the interfering common-mode currents and is designed for measuring common-mode currents, by measuring a current on a path from a potential V of the ECG component 501 by way of a parasitic capacitance or a protection capacitor designed for ESD protection, represented in FIG. 5 as impedance IM, to ground E.

The signal measuring circuit 502, also known as the ECG measuring circuit, includes a first electrode 1, which is connected by its input to a patient P. The first electrode 1 is part of a first measuring path MP1, which includes the first electrode 1. The ECG measuring circuit 502 includes a second electrode 2, which is likewise electrically connected by its input to the patient P. The second electrode 2 is in this case part of a second measuring path MP2.

The signal measuring circuit 502 includes an amplifier circuit 4, which has a first input 5 and a second input 6 and also an output 7. The amplifier circuit 4 is connected by its first input 5 to the first electrode 1 and is electrically connected by its second input 6 to the second electrode 2. The output 7 of the amplifier circuit 4 is connected to an input of a first signal detection unit 21.

Depicted at the bottom right in FIG. 5 is the second measuring circuit, e.g., the interference-signal measuring circuit 503 for measuring the interfering common-mode currents. The second measuring circuit 503 is not connected directly to the ECG measuring circuit 502, but only by way of a reference potential V, which is also referred to as potential V of the ECG component. The potential V may, for example, be the potential of the housing of the measuring circuit 500 of the ECG component.

As may be seen in FIG. 5, in the interference-signal measuring circuit 503 a current IE flows from the reference potential V by way of an impedance IM and by way of an additional capacitance C to ground E. The impedance IM serves the purpose of converting the current flowing to ground E into an electrical voltage that may be measured by the interference-signal measuring circuit 503. The additional capacitance C may include, for example, a parasitic capacitance, a capacitor or, in particular, an ESD protection capacitor.

The interference-signal measuring circuit 503 includes a measuring amplifier 8 with a first input 9 and a second input 10 and an output 11. The first input 9 of the measuring amplifier 8 is electrically connected to the end of the impedance IM that is at the reference potential V and the second input 10 of the interference-signal measuring circuit 503 is electrically connected to the end of the impedance IM that is arranged on the ground side. The output of the interference-signal measuring circuit 503 is electrically connected to a second signal detection unit 22. So if a current $I_E$ flows from the potential V of the ECG component in the direction of ground E, this may be measured with the aid of the interference-signal measuring circuit 503.

The current $I_E$ flowing by way of the additional current path is advantageously stronger by several orders of magnitude than the current $I_{CM}$ through the first measuring path MP1 and the second measuring path MP2. Moreover, a measurement in the additional current path also has no influence on the input circuitry. Such a circuit also functions when using what is known as a right-leg drive (or driver circuit for the right leg), also known as the RLD path for short. In this case, the current IE flowing to ground may have a value higher by one to three orders of magnitude than the current flowing through the measuring paths MP1, MP2. As already mentioned, in the case of the signal measuring circuit 400 depicted in FIG. 4, although the measuring path for measuring the common-mode currents or common-mode signals is already not directly in the signal measuring circuit, it is still in the range of influence of the analog input circuitry. In the case of the circuit arrangement 500 in FIG. 5 according to an exemplary embodiment, on the other hand, the measuring path 503 for the measurement of the common-mode signals is now only sharing the common reference potential with the signal measuring circuit 502, and is consequently decoupled to the maximum, which advantageously leads to a minimization, if not complete elimination, of the interference of the ECG measuring paths by the measurement of the common-mode currents.

Figure 6:
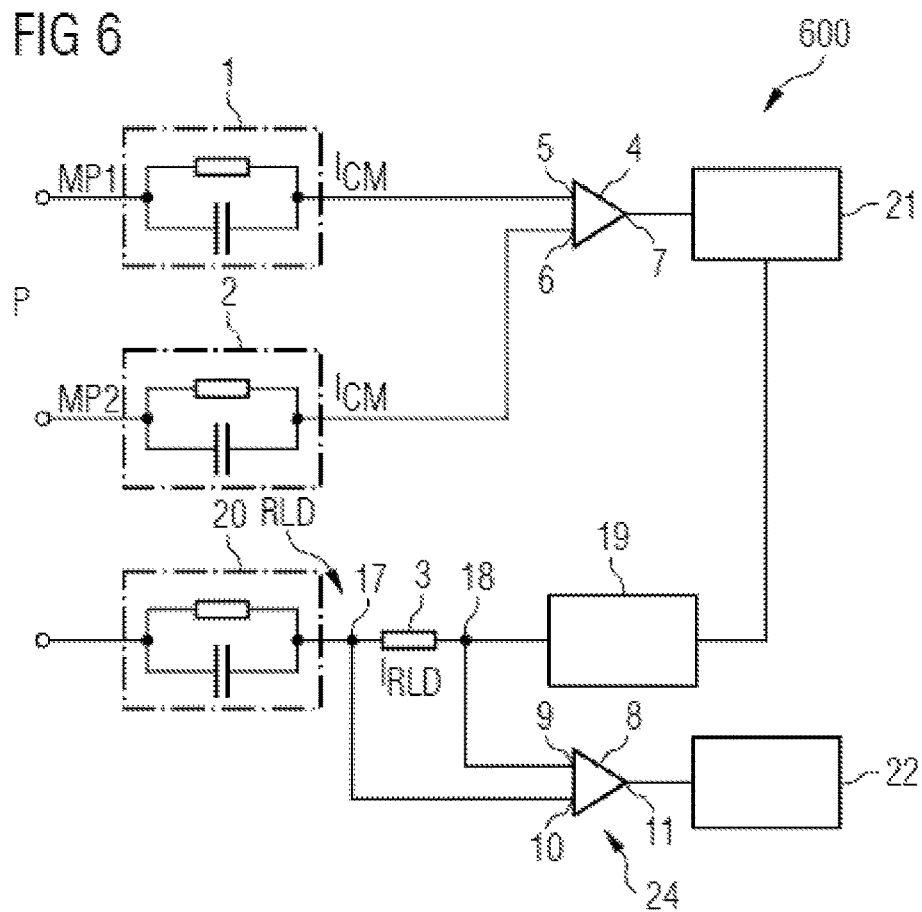
FIG. 6 schematically depicts a differential voltage measuring system according to a second exemplary embodiment.

In FIG. 6, there is schematically depicted a differential voltage measuring system 600, for example, an ECG measuring circuit, in which the common-mode current is measured in a separate current path, which is formed as an RLD path. In such a current path there flows a current $I_{RLD}$, which is about one to three orders of magnitude greater than the currents $I_{cm}$ through the first measuring path MP1 and through the second measuring path MP2 of the measuring circuit 600. In a way similar to the measuring circuit depicted in FIG. 5, the measuring circuit 600 depicted in FIG. 6 includes a first measuring path MP1 with a first electrode 1, which is connected by its input to a patient P, and a second measuring path with a second electrode 2, which is likewise electrically connected by its input to the patient P.

The measuring circuit 600 depicted in FIG. 6 has moreover an amplifier circuit 4, which includes a first input 5 and a second input 6 and also an output 7. The amplifier circuit 4 is electrically connected by its first input 5 to the first electrode 1 and electrically connected by its second input 6 to the second electrode 2. The output 7 of the amplifier circuit 4 is electrically connected to an input of a first signal detection unit 21.

In addition, the first signal detection unit 21 is connected to a driver circuit 19, also referred to as a right-leg drive. The driver circuit 19 is connected by way of an additional path RLD to an additional contact 20 with the patient P. The patient P is set to a reference potential by way of the additional path, also referred to as the RLD path. The driver circuit 19 serves for generating a signal that may be controlled to the average common-mode voltages of individual signals or all the signals or may be set to a fixed voltage value. In addition, a shunt resistor 3 is arranged between the driver circuit 19 and the path 20. The voltage dropping across the shunt resistor 3 is determined by a voltage measuring device 24. The voltage measuring device 24 includes a second amplifier circuit 8, which measures a voltage dropping across the shunt resistor 3 and passes it on to a second signal detection unit 22. The second amplifier circuit 8 likewise includes a first input 9 and a second input 10 and also an output 11. The first input 9 is connected to the end 18 of the shunt resistor 3 that is facing the driver circuit 19, and the second input 10 is connected to the end 17 of the shunt resistor 3 that is facing the patient P. The output 11 of the second amplifier circuit 8 is electrically connected to a second signal detection circuit 22. With the aid of the second amplifier circuit 8, the voltage dropping across the shunt resistor 3, and consequently the common-mode current as a component of the current $I_{RLD}$ through the RLD path RLD, is measured.

The overall impedance of the RLD path RLD is scarcely influenced by the shunt resistor 3, since it is relatively small in comparison with the patient protection resistors and the electrode transfer resistance. Values for the shunt resistor may be in the range of 10-100 kΩ The resistance values of the patient protection resistors may lie in the range from 100 kΩ to 500 kΩ; values for the electrode transfer resistances may be in the range from 10 kohms to 2 Mohms.

Figure 7:
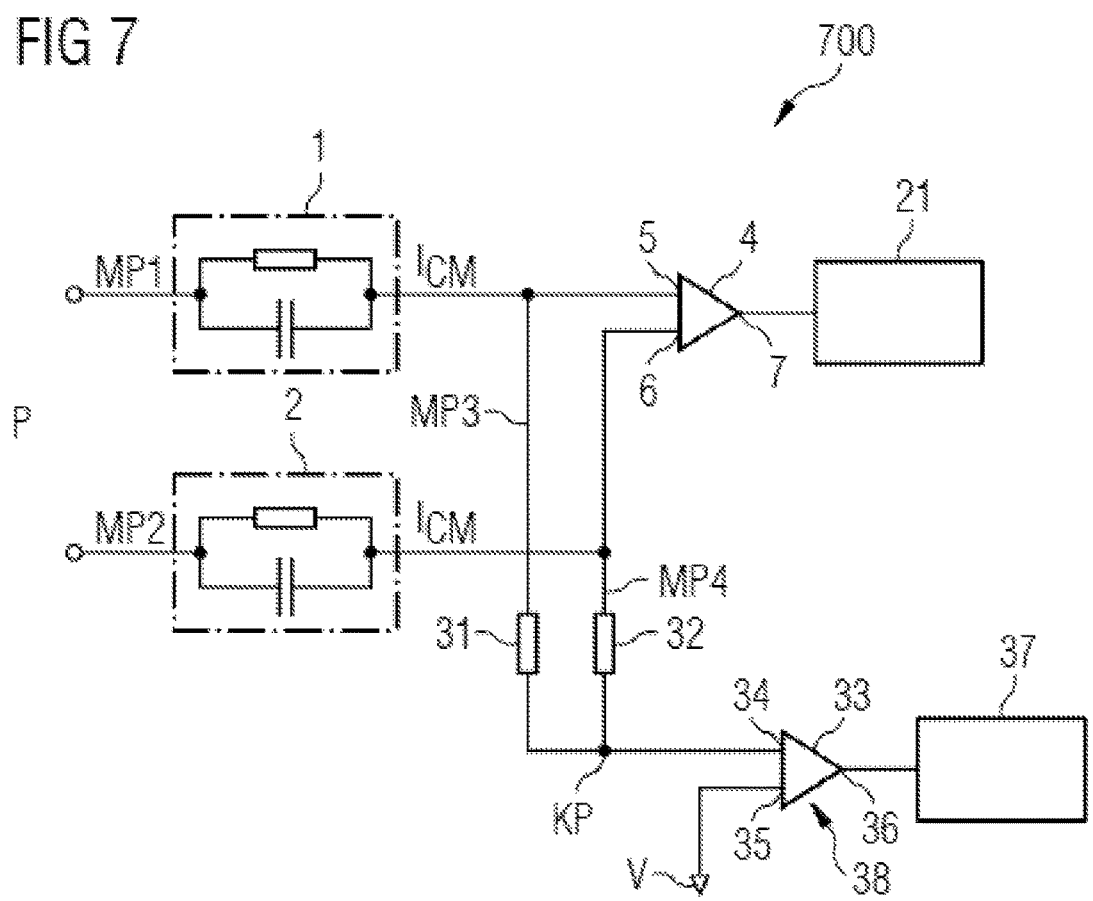
FIG. 7 schematically depicts a differential voltage measuring system according to a third exemplary embodiment.

In FIG. 7, a differential voltage measuring system 700 according to a third exemplary embodiment is schematically depicted. In a way similar to the measuring circuits 500, 600 depicted in FIGS. 5 and 6, the system 700 includes a first measuring path MP1 with a first electrode 1, which at the input is connected to a patient P and at the output provides a first measuring contact, and a second measuring path MP2 with a second electrode 2, which at the input is connected to the patient P and at the output provides a second measuring contact.

A first amplifier circuit 4 is electrically connected by its first input 5 to the first measuring path MP1, is electrically connected by its second input 5 to the second measuring path MP2 and is electrically connected by its output 6 to a first signal detection unit 21. In addition, the system 700 includes a potential measuring unit 38, which is designed for determining an average value from a potential at the first measuring path MP1 between the first electrode 1 and the first input 4 of the first amplifier circuit 3 and a potential at the second measuring path MP2 between the second electrode 2 and the second input 6 of the first amplifier circuit 4. For this purpose, the potential measuring unit 38 includes two additional third and fourth measuring paths MP3, MP4 with resistors 31, 32, which are connected to the first measuring path MP1 and the second measuring path MP2, respectively, and are connected in parallel with one another by way of a contact point KP.

From this circuitry, an average potential results at the contact point KP. This averaging has the advantage of thereby eliminating differential components caused by the different quality of the contacts of the electrodes 1, 2 of the first and second measuring paths MP1, MP2 at the common contact point KP. The averaged potential at the common contact point KP is measured by a second amplifier circuit 33, which is part of the potential measuring unit 38. The second amplifier circuit 33 has a first input 34, a second input 35 and also an output 36, the averaged potential being present at the first input 34. The second amplifier circuit 33 compares the averaged potential with a reference potential V at its second input and transmits the measured signal by way of its output 36 to a signal detection device 37. The reference potential at the second input may, for example, be the potential of the ECG input circuit. The potential of the ECG input circuit is in fact freely floating; it is very isolated from the ground. Connected to the patient, the potential assimilates to the patient. The common-mode current flows until the ECG component is at the potential of the patient. Since the ECG component and the patient are never connected by way of a resistance of 0 ohm, the potential of the component and the patient is never the same—a voltage drops across this resistance due to the common-mode current. This voltage is the difference between the potential of the patient and the ECG component.

Finally, it is once again pointed out that the previously described detailed methods and devices are exemplary embodiments and that the basic principle may also be varied by a person skilled in the art within broad ranges without departing from the scope of the invention, to the extent prescribed by the claims.

It is also pointed out for the sake of completeness that the use of the indefinite article "a" or "an" does not exclude the possibility that the features concerned may also be multiply present. Similarly, the term "unit" does not exclude the possibility that it consists of multiple components, which may possibly also be spatially distributed.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification. While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A differential voltage measuring system comprising:
   a housing;
   a signal measuring circuit positioned within the housing, the signal measuring circuit configured to measure bioelectric signals; and
   an interference-signal measuring circuit positioned within the housing, the interference-signal measuring circuit coupled to a potential of the differential voltage measuring system and electrically connected to a fixed reference potential,
   wherein the interference-signal measuring circuit is configured for measuring a current flowing from the potential of the differential voltage measuring system to the fixed reference potential, and
   wherein the potential of the differential voltage measuring system is a potential of the housing.

2. The differential voltage measuring system of claim 1, wherein an impedance is connected between the potential of the differential voltage measuring system and the fixed reference potential.

3. The differential voltage measuring system of claim 2, wherein the interference-signal measuring circuit comprises:
   an amplifier circuit comprising a first input electrically connected to an end of the impedance facing the potential of the differential voltage measuring system, a second input electrically connected to an end of the impedance facing the fixed reference potential, and an output; and
   a signal detection unit at the output of the amplifier circuit.

4. The differential voltage measuring system of claim 3, further comprising:
   a capacitance comprising an element with a parasitic capacitance or an electrostatic discharge (ESD) protection capacitor, the capacitance having a capacitance value of less than 10 pF, or a combination thereof, wherein the capacitance is connected between the impedance and the fixed reference potential.

5. The differential voltage measuring system of claim 2, further comprising:
   a capacitance comprising an element with a parasitic capacitance or an electrostatic discharge (ESD) protection capacitor, the capacitance having a capacitance value of less than 10 pF, or a combination thereof, wherein the capacitance is connected between the impedance and the fixed reference potential.

6. The differential voltage measuring system of claim 1, further comprising:
   a first measuring path comprising a first electrode, wherein an input of the first measuring path is connected to a patient and an output of the first measuring path provides a first measuring contact;
   a second measuring path comprising a second electrode, wherein an input of the second measuring path is connected to the patient and an output of the second measuring path provides a second measuring contact;
   an amplifier circuit comprising a first input electrically connected to the first measuring path, a second input electrically connected to the second measuring path, and an output; and
   a first signal detection unit at the output of the amplifier circuit.

7. The differential voltage measuring system of claim 6, further comprising:
   a further contact with the patient for generating a signal configured to be controlled to average common-mode voltages of individual signals or all signals or configured to be set to a fixed voltage value.

8. A differential voltage measuring system comprising:
   a first measuring path comprising a first electrode, wherein an input of the first measuring path is connected to a patient and an output of the first measuring path provides a first measuring contact;
   a second measuring path comprising a second electrode, wherein an input of the second measuring path is connected to the patient and an output of the second measuring path provides a second measuring contact;
   an amplifier circuit comprising a first input electrically connected to the first measuring path, a second input electrically connected to the second measuring path, and an output;
   a signal detection unit at the output of the amplifier circuit;
   an additional path comprising a contact with the patient, the additional path having a driver circuit for a right leg, a shunt resistor with a known resistance value, wherein the additional path is connected between an additional contact and the driver circuit; and
   a voltage measuring device connected parallel to the shunt resistor and having an electrical voltage dropping across the shunt resistor, the voltage measuring device configured to measure a current flowing between the additional contact and the driver circuit.

9. The differential voltage measuring system of claim 8, wherein the shunt resistor comprises a resistance value in a range of 10-100 kΩ.

10. The differential voltage measuring system of claim 8, wherein the voltage measuring device comprises an amplifier circuit having a first input electrically connected to an end of the shunt resistor facing the driver circuit, and a second input electrically connected to an end of the shunt resistor facing the additional contact to the patient, and an output.

11. The differential voltage measuring system of claim 10, wherein the voltage measuring device comprises a signal detection unit electrically connected to the output of the amplifier circuit of the voltage measuring device.

12. A differential voltage measuring system comprising:
    a first measuring path comprising a first electrode, wherein an input of the first measuring path is connected to a patient and an output of the first measuring path provides a first measuring contact;

a second measuring path comprising a second electrode, wherein an input of the second measuring path is connected to the patient and an output of the second measuring path provides a second measuring contact;

an amplifier circuit comprising a first input electrically connected to the first measuring path, a second input electrically connected to the second measuring path, and an output;

a signal detection unit at the output of the amplifier circuit; and a potential measuring unit designed for determining an average value from a potential at the first measuring path between the first electrode and the first input of the amplifier circuit and a potential at the second measuring path between the second electrode and the second input of the amplifier circuit, wherein the potential measuring unit comprises two parallel-connected potential measuring paths and an amplifier circuit having a first input, a second input, and an output, wherein the first input of the amplifier circuit of the potential measuring unit is electrically connected to the branching point of the parallel-connected potential measuring paths and the second input of the amplifier circuit of the potential measuring unit is electrically connected to a reference potential, and wherein the reference potential is the potential of an electrocardiogram input circuit.

13. The differential voltage measuring system of claim 12, wherein the first potential measuring path comprises (1) a first contact between the first electrode and the first input of the amplifier circuit and (2) a first resistor, wherein the second potential measuring path comprises (1) a second contact between the second electrode and the second input of the amplifier circuit and (2) a second resistor, and wherein the two parallel-connected measuring paths are brought together to a common averaged potential at a branching point of the parallel-connected measuring paths.

14. The differential voltage measuring system of claim 13, wherein the potential measuring unit is designed for determining an averaged differential signal of the measuring paths and of the reference potential.

15. The differential voltage measuring system of claim 14, wherein the potential measuring unit further comprises a signal detection unit electrically connected to the output of the amplifier circuit of the potential measuring unit.

16. The differential voltage measuring system of claim 15, further comprising an additional patient contact with a driver circuit for a right leg, wherein the potential measuring unit further comprises an additional potential measuring path between the additional patient contact and the branching point, wherein a potential at the additional patient contact is taken into account in the determination of the averaged potential.

17. The differential voltage measuring system of claim 12, wherein the potential measuring unit is designed for determining an averaged differential signal of the measuring paths and of the reference potential.

18. The differential voltage measuring system of claim 12, wherein the potential measuring unit further comprises a signal detection unit electrically connected to an output of an amplifier circuit of the potential measuring unit.

19. The differential voltage measuring system of claim 12, further comprising an additional patient contact with a driver circuit for a right leg, wherein the potential measuring unit further comprises an additional potential measuring path between the additional patient contact and the branching point, wherein a potential at the additional patient contact is taken into account in the determination of the averaged potential.

* * * * *